United States Patent [19]

Goethel

[11] Patent Number: 4,695,271
[45] Date of Patent: Sep. 22, 1987

[54] ANGIOGRAPHIC INJECTOR

[75] Inventor: James H. Goethel, Cincinnati, Ohio

[73] Assignee: Liebel-Flarsheim Company, Cincinnati, Ohio

[21] Appl. No.: 825,473

[22] Filed: Feb. 3, 1986

[51] Int. Cl.⁴ ............................................. A61M 5/20
[52] U.S. Cl. .................................... 604/49; 604/122; 604/154; 128/DIG. 1
[58] Field of Search .................. 604/52, 67, 122, 123, 604/154, 155; 128/DIG. 1; 222/47, 49, 63

[56] References Cited

U.S. PATENT DOCUMENTS 4,465,474 8/1984 Mardorf et al. ..................... 604/154
4,560,979 12/1985 Rosskopf ........................ 604/154 X Primary Examiner—Stephen C. Pellegrino
Attorney, Agent, or Firm—Marjama & Pincelli

[57] ABSTRACT

A method and apparatus for injecting a contrast media having means for preventing, operation thereof until the plunger of a syringe cartridge has been first placed in the fully extended position.

9 Claims, 5 Drawing Figures

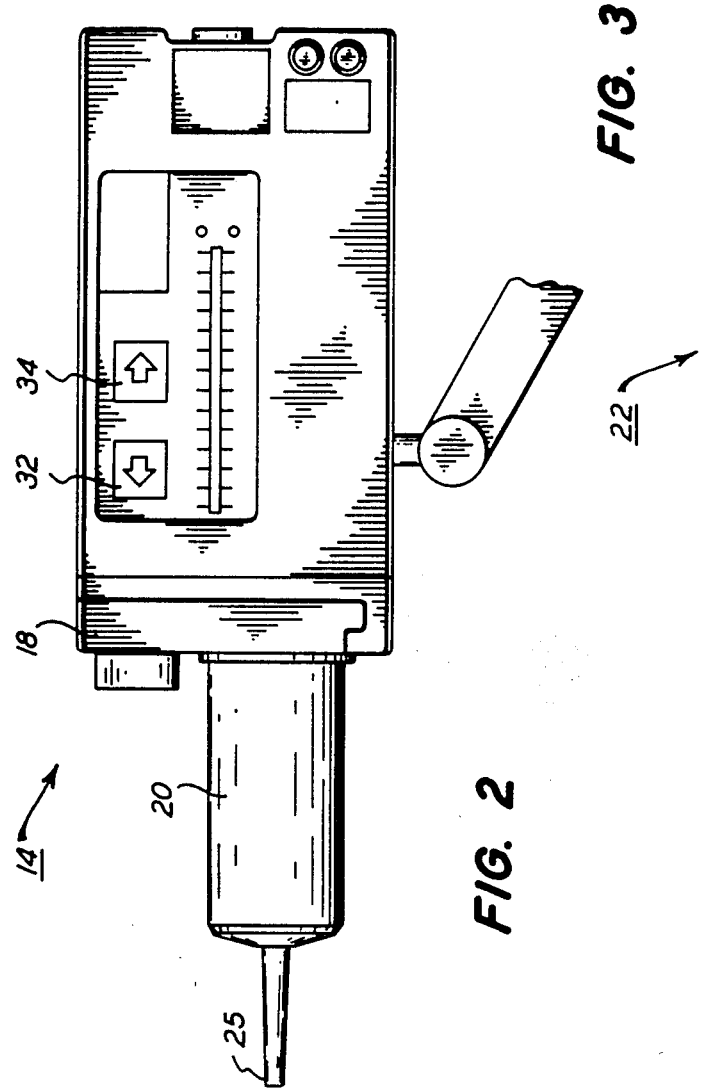
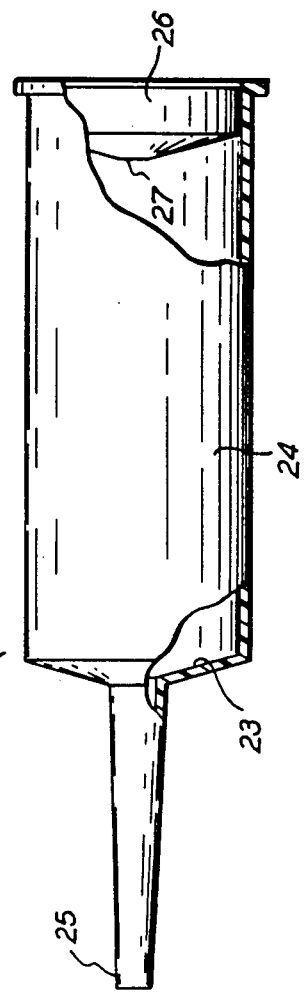
FIG. 2
FIG. 3

ANGIOGRAPHIC INJECTOR

The foregoing abstract is not to be taken as limiting the invention of this application, and in order to understand the full nature and extent of the technical nature of this application, reference must be made to the accompanied drawings and the following detailed description.

BACKGROUND OF THE INVENTION

This invention relates, in general, to the medical science of angiography, and more particularly to an improved angiographic injector.

Angiography is a radiological technique wherein the arteries or veins of the human or animal body are outlined by injecting a suitable contrast media thereby, permitting x-ray photographs to be made of the veins or arteries into which material has been injected. Precautions are normally taken by operating personnel to remove any air bubbles from the syringe. On rare occasions, the operator forgets to load any contrast media into the syringe resulting in injection of air.

The angiographic injector of the present invention minimizes the possibility of injecting air into a human or animal body.

SUMMARY OF THE PRESENT INVENTION

The present invention is directed to a method and apparatus for injecting a contrast media wherein means are provided for preventing operation of the injector until plunger in the syringe is first placed in the fully extended position.

DESCRIPTION OF FIGURES

FIG. 2 is a side elevation view of the power head of the injection apparatus of FIG. 1;

FIG. 3 is a side elevation view of a cartridge for use in the power head of FIG. 2;

DESCRIPTION OF THE PREFERRED EMBODIMENT

Figure 1:
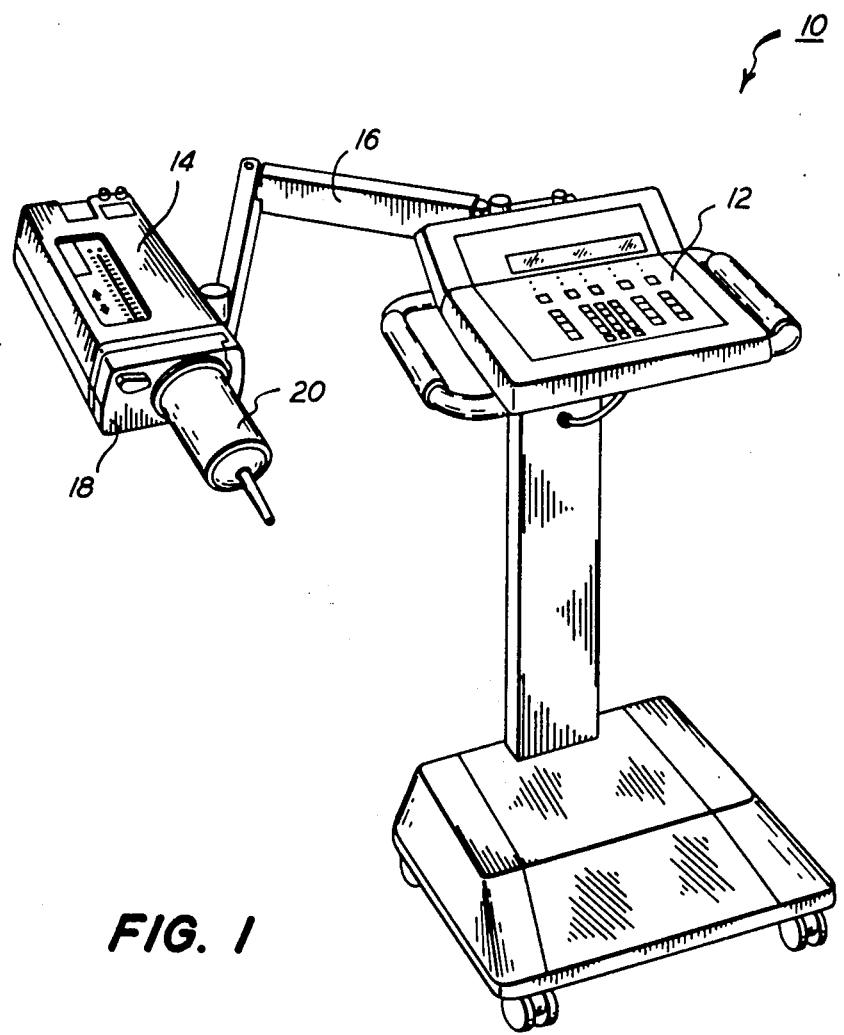
FIG. 1 is a pictoral view of an injection apparatus constructed according to the present invention.

Referring to FIG. 1, there is illustrated an injection apparatus 10 made in accordance with the present invention comprising a control console 12 for selecting and controlling the operation of the injection power head 14. The injection power head 14 is connected to control console 12 by hinged arm 16 which allows the injection power head 14 to be disposed in any desired position.

Figure 4:
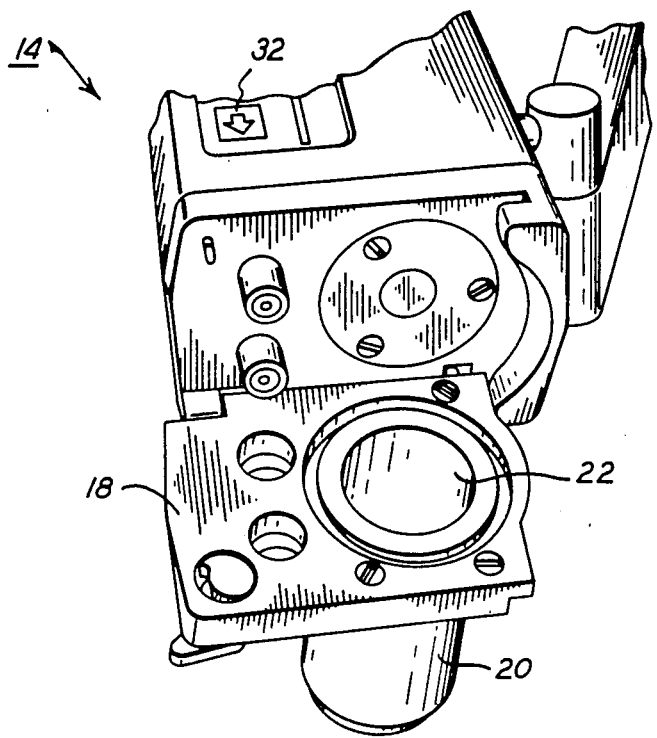
FIG. 4 is a fragmentary perspective view of the power head of FIG. 2 with the access door in the open position.

Referring to FIGS. 2, 3, 4 and 5, the injection power head 14 is shown in greater detail. The front portion of injection power head 14 is provided with an access door 18. The access door 18 has a receiving chamber 20 for accepting a syringe cartridge 22 when the access door 18 is in the open position as illustrated in FIG. 4.

Syringe cartridge 22 (see FIG. 3) comprises an outer shell 24 having an integrally formed injection port 25 at one end. A slidable plunger 26 is disposed within the outer shell 24. The syringe 22 is normally empty when purchased and is filled after placement in receiving chamber 20. The side 27 of plunger 26 which faces port 25 has a configuration shaped so as to conform to mating surface 23 of cartridge 22.

Figure 5:
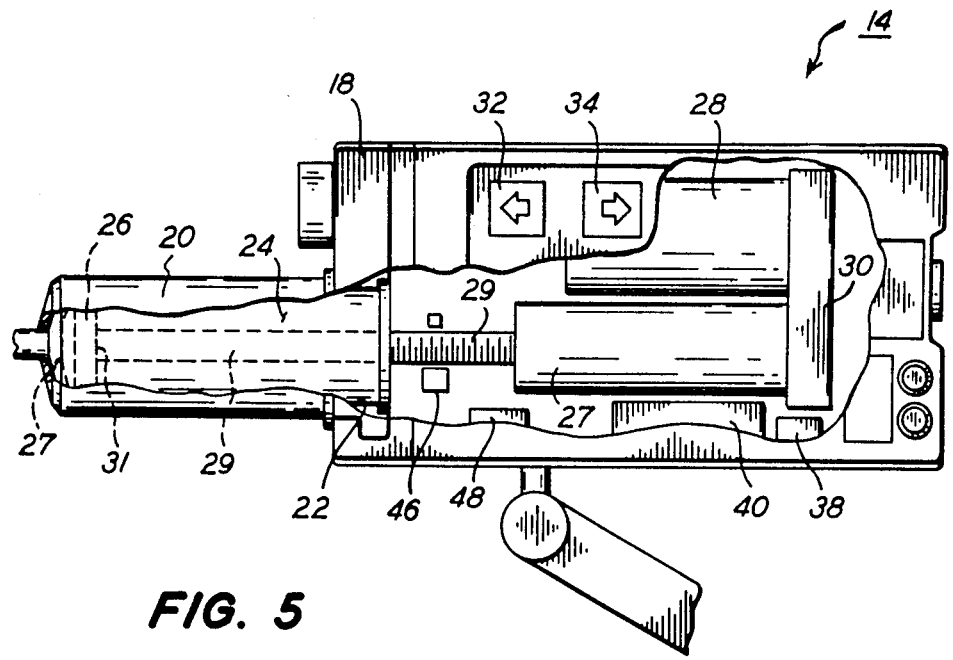
FIG. 5 is a cut-away schematic view of the power head of FIG. 2.

FIG. 5 illustrates a cross-sectional view of the power head 14 with a syringe cartridge 22 placed therein. Injection power head 14 is provided with a plunger drive 27 which is capable of being connected to plunger 26 of syringe cartridge 22. In the present invention, the plunger drive 27 is connected to motor 28 through gear box 30 and is appropriately activating either forward by switch 32 or reverse by switch 34. The plunger drive 27 is connected to plunger 26 by screw shaft 29. The end 31 of screw shaft 29 is designed to mate with plunger 26 so as to allow plunger drive 27 to easily slide plunger 26 along the longitudinal axis of shell 24.

Means are provided for providing a signal when the plunger 26 has been fully extended. In the particular embodiment illustrated, a limit switch 46 sends a signal to the microprocessor signaling that the plunger has been fully extended whereby the microprocessor sends the appropriate signal to turn off the motor and prevent any further extension of the plunger 26. In the particular embodiment illustrated limit switch 46 comprises an optical switch which produces a signal upon the sensing of a flag. While in the preferred embodiment a limit switch 46 is used, other sensing means may be used. For example, a linear potentiometer 38 may be used to sense the position of the screw shaft which in turn is related to the position of the plunger 26.

The microprocessor 40 is programmed such that the injection power head 14 cannot be placed in the "armed" state until the plunger 26 has been fully extended as illustrated in FIG. 5 by dash lines. For the purposes of this invention, the "armed" state is that condition which will allow the injection power head to dispense contrast media, commonly referred to as the injection mode. By requiring the operator to run the plunger 26 to the fully extended position before the injector can be placed in the armed state, it is likely that the operator will then draw contrast media into the syringe when the plunger is drawn back. An over ride feature may be incorporated to arm the injector should a prefilled syringe be used, however, this requires a specific overt act by the operator.

A mercury switch 48 is provided for determining the vertical position of syringe cartridge 22 in receiving chamber 20. When the syringe cartridge 32 is in the vertical position, that is, when injection port 25 is pointed substantially vertically upward, the mercury switch sends a signal to the microprocessor 40. In the preferred embodiment, the microprocessor is programmed such that the plunger must be extended to its fully extended position when the syringe cartridge is pointed substantially vertically up. This further minimizes the possibility of trapping air in the syringe. However, the mercury switch may be omitted, if desired.

The microprocessor 40 is programmed such that the plunger must go through the fully extended cycle each time the injection has been powered up. For the purposes of this invention the term "powered up" shall mean when either electrical or mechanical power necessary to drive the power head is first available, for example, when the access door is opened for any reason. Therefore, means have been provided for preventing operation of the injection power head in the injection mode until the plunger 26 has been fully extended after the injector power has either been powered up or the access door opened.

While certain representative embodiments and details have been shown and described for the purpose of describing the invention, it will be apparent that various changes or modifications may be made without departing from the scope of the invention.

What is claimed is:

1. An apparatus having a powerhead for injecting a fluid into a living being comprising:
    a. receptacle means mounted to said power head for receiving and holding a syringe cartridge having a movable plunger;
    b. means mounted to said power head for moving said plunger along the longitudinal axis of said syringe cartridge;
    c. means mounted to said power head for determining when said plunger had been fully extended; and
    d. means associated with said power head for preventing operation of said power head in the injection mode until said plunger has been fully extended after said power head has been powered up or when a new cartridge has been placed in said receptacle means.

2. An apparatus according to claim 1 wherein said means for preventing operation of said power head in the injection mode until said plunger has been fully extended comprises switch means which produces a signal when said plunger has been placed in the fully extended position.

3. An apparatus having a power head for injecting a fluid into a living being comprising:
    a. receptacle means mounted to said power head for receiving and holding a syringe cartridge having a slidable plunger;
    b. means mounted to power head for moving said plunger along the longitudinal axis of said syringe cartridge;
    c. means associated with said power head for preventing operation of said power head in the injection mode untIl said plunger has been fully extended after said power head has been powered up or when a new cartridge has been placed in said receptacle means.

4. An apparatus according to claim 3 wherein said means for preventing operation of said power head in injection mode until said plunger has been fully extended comprises switch means positioned such that a signal is produced wherein said plunger is disposed in the fully extended position.

5. An apparatus according to claim 4 further comprising means mounted to said power head for determining the vertical position of said syringe cartridge, means for preventing operation of said power head unless said syringe cartridge has been positioned such that the injection part is positioned in a substantially upward vertical direction prior to having said plunger extended to the fully extended position.

6. An apparatus according to claim 5 wherein said means for determining the vertical position of said syringe cartridge comprises a mercury switch having two electrical contacts which will be in a closed position when said syringe cartridge is in a substantially vertical position.

7. Method for minimizing accidental injection of air into a living being by an apparatus used for injecting a fluid into said living being, said apparatus having a receptacle for receiving and holding a syringe cartridge having a movable plunger, comprising the following sequence of steps:
    a. placing a syringe cartridge in said receptacle;
    b. positioning said apparatus such that said syringe cartridge is pointed in a substantially vertical upward position;
    c. causing said plunger to go into the fully extended position;
    d. providing means to prevent operation of said apparatus in the injection mode until said foregoing steps have been completed after power has been provided to said apparatus or a new cartridge has been placed in said receptacle.

8. Method for minimizing accidental injection of air into a living being by an apparatus used for injecting a fluid into said human being, said apparatus having a receptacle for receiving and holding a syringe cartridge having a movable plunger, comprising the following sequence of steps:
    a. placing a syringe cartridge in said receptacle;
    b. causing said plunger to go into the fully extended position;
    c. providing means to prevent operation of said apparatus in the injection mode until said foregoing steps have been completed after power has been provided to said apparatus or a new cartridge has been placed in said receptacle.

9. Method according to claim 8 further comprises steps of positioning said device such that said syringe is pointed in a substantially vertical position prior to causing said plunger to go into the fully extended position.

* * * * *